US007224282B2

(12) United States Patent
Terauchi et al.

(10) Patent No.: US 7,224,282 B2
(45) Date of Patent: May 29, 2007

(54) CONTROL APPARATUS AND METHOD FOR CONTROLLING AN ENVIRONMENT BASED ON BIO-INFORMATION AND ENVIRONMENT INFORMATION

(75) Inventors: Toshiro Terauchi, Tokyo (JP); Yoichiro Sako, Tokyo (JP); Akiko Inoue, Saitama (JP); Makoto Inoue, Kanagawa (JP); Katsuya Shirai, Kanagawa (JP); Yasushi Miyajima, Kanagawa (JP); Kenichi Makino, Kanagawa (JP); Motoyuki Takai, Tokyo (JP)

(73) Assignee: Sony Corporation (JP)

( * ) Notice: Subject to any disclaimer, the term of this patent is extended or adjusted under 35 U.S.C. 154(b) by 142 days.

(21) Appl. No.: 10/862,657

(22) Filed: Jun. 7, 2004

(65) Prior Publication Data
US 2004/0263337 A1 Dec. 30, 2004

(30) Foreign Application Priority Data
Jun. 30, 2003 (JP) ............................ P2003-188420

(51) Int. Cl.
*G08B 23/00* (2006.01)
*G09B 21/00* (2006.01)
(52) U.S. Cl. ................................ 340/573.1; 340/825.19
(58) Field of Classification Search ............. 340/573.1, 340/825.19, 870.16, 870.17, 146.2, 500, 340/501, 539.26, 539.29; 600/306, 307, 600/346, 372, 382, 391, 481, 484, 485, 500, 600/502, 503, 508, 509, 529
See application file for complete search history.

(56) References Cited

U.S. PATENT DOCUMENTS

| 6,084,516 | A | * | 7/2000 | Yasushi et al. | ........... 340/573.1 |
|---|---|---|---|---|---|
| 6,198,394 | B1 | * | 3/2001 | Jacobsen et al. | .......... 340/573.1 |
| 6,348,867 | B1 | * | 2/2002 | Myllymaki | ............... 340/573.1 |
| 6,607,484 | B2 | * | 8/2003 | Suzuki et al. | ................ 600/300 |
| 2001/0056225 | A1 | * | 12/2001 | DeVito | ......................... 600/300 |
| 2005/0001728 | A1 | * | 1/2005 | Appelt et al. | ............. 340/573.1 |

\* cited by examiner

*Primary Examiner*—Daniel Wu
*Assistant Examiner*—Jennifer Mehmood
(74) *Attorney, Agent, or Firm*—Lerner, David, Littenberg, Krumholz & Mentlik, LLP

(57) ABSTRACT

A sound, a video and/or other environments are proposed in tune with the physical condition of a user and a peripheral environmental condition such that it becomes possible for users to feel comfortable and to be satisfied with their sensibility. It is designed to produce an objective sound, video and/or other environments by inputting bio-information of a user such as breathing, pulse-beats and heartbeats or environment information such as weather, date and hour and ambient temperature, by comparing information with the accumulated information utilized in the past, or by setting a condition that the user desires.

10 Claims, 5 Drawing Sheets

Example of bio-information measuring

Constitutional example

Example of bio-information measuring

Example of output providing apparatus

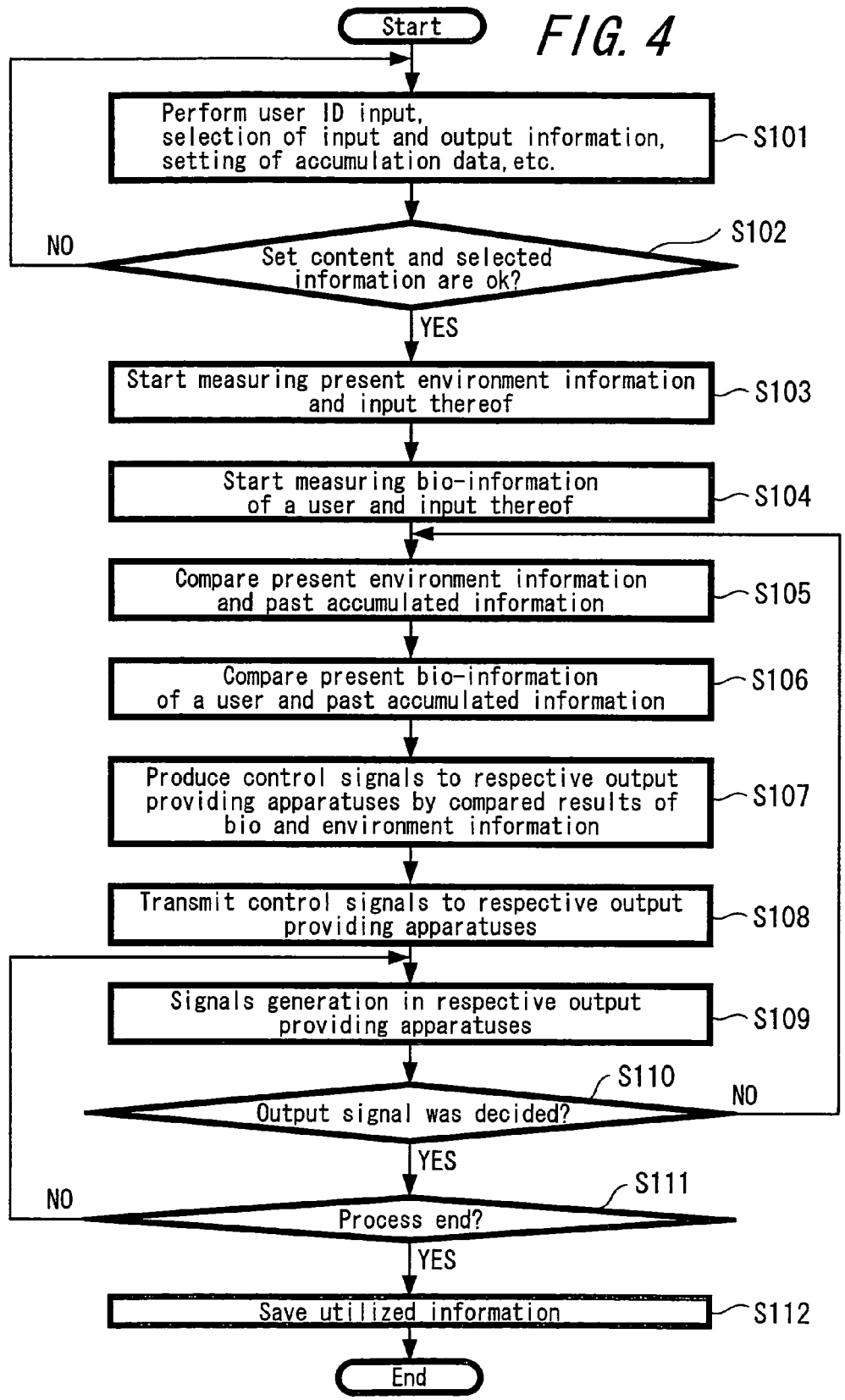
Process example 1 of controlling output providing apparatus

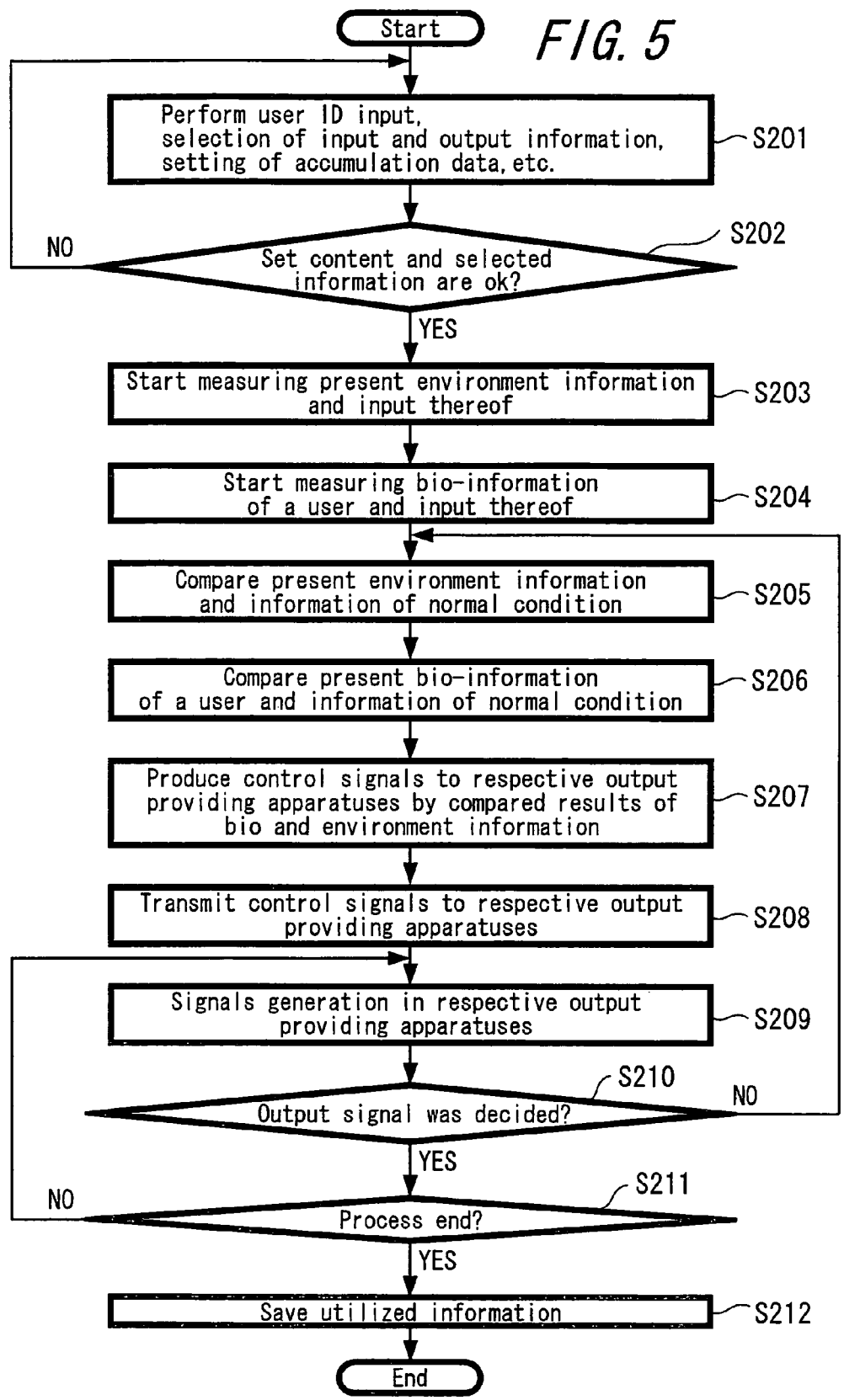
Process example 2 of controlling output providing apparatus

US 7,224,282 B2

CONTROL APPARATUS AND METHOD FOR CONTROLLING AN ENVIRONMENT BASED ON BIO-INFORMATION AND ENVIRONMENT INFORMATION

BACKGROUND OF THE INVENTION

1. Field of the Invention

The present invention relates, for example, to a control apparatus for controlling a condition of a user and a periphery environment by using bio-information of a user such as breathing, pulse-beats and heartbeats and environment information such as weather, date and hour and ambient temperature and further relates to its control method.

2. Description of the Related Art

Heretofore, it has been known an audio system, a television, a video apparatus and the like as an acoustic and a video apparatus. These and reproduce information recorded on a recording medium beforehand and also receive and reproduce information distributed by means of an electric wave and the like, but in any of them, users themselves should select a desired sound and/or video content and the reproducing condition of the sound volume, the sound quality, the brightness of the video and the like was to be adjusted when it is necessary.

In recent years, an environment adaptive type acoustic apparatus has been proposed where music can be enjoyed pleasantly by detecting bio-information of a resident even though an aged person and a physically handicapped person resides in any part of a room. According to this apparatus, it is controlled such that the condition becomes the most optimal one fit with this physical condition of a resident by properly adjusting the sound quality, the volume of the sound or the like according to the bio-information of a resident. Also, it is possible to reproduce preferable music of a resident corresponding to his physical condition by judging what a content the resident listens to preferably in what a situation according to the physical condition of the resident and at the same time according to the living environment condition, for example, such as date and hour, weather and a number of indoor people.

In a patent reference 1, there is shown with respect to an environment adaptive type acoustic apparatus mentioned above.

<Patent Reference 1>

Japanese Laid-open Patent No. 11-221196

However, in the prior art an environment adaptive type acoustic apparatus mentioned above, it is possible to propose music suitable for a present physical condition of a user, but there was a problem that it was not consider about a condition which a user feels comfortable and the degree of his satisfaction. For example, it was not possible to make a user be a relaxed state of mind by easing his tension in a case when a user is in a state of tension before going to bed or make his physical condition be activated in a case when an activity level of a user is low in the morning. Therefore, the sensibility of a user could not be satisfied as a result.

SUMMARY OF THE INVENTION

In view of the aforesaid problem, the object of the present invention lies in that it is made possible for a user to feel comfortable and for his sensibility to be satisfied by proposing a sound a video and other environments in tune with a physical condition of a user and a periphery environment condition.

According to the present invention, a target sound, video, and/or periphery environment is produced by inputting bio-information such as breathing, pulse-beats and heartbeats of a user or by inputting environment information such as weather, date and hour and ambient temperature and by comparing those of the information with past utilized information which was accumulated and alternatively by setting a condition which a user desires.

In this manner, it becomes possible to offer a music, a video, other environments and the like which a user desires such that the sensibility of the user will be satisfied without performing a detailed setting and a complicated adjusting operation by the user.

Hereinafter, one exemplified embodiment of the present invention will be explained with reference to FIG. 1 to FIG. 5. It should be noted in this example that information showing heartbeats, pulse-beats, breathing, blood pressure, SpO2 (Blood Oxygen Saturation), electrocardiograms, brain waves, sweating of skin, GSR (Galvanic Skin Response), body movement, MEG (Magnetoencephalography), EMG (Electro-Myography), body surface temperature, diameter size of a pupil, micro-vibration, biochemical reaction and the like will be designated as bio-information. Also, natural information such as date and hour, lunar age, ambient temperature, humidity, weather, atmospheric pressure and the ebb and flow of tide and environment information such as ambient noise, room temperature and a smell will be designated as circumference environment information.

BRIEF DESCRIPTION OF THE DRAWINGS

FIG. 4 is a flowchart showing a control process of an output providing apparatus an exemplified embodiment of the present invention; and FIG. 5 is a flowchart showing a control process of an output providing apparatus another exemplified embodiment of the present invention.

DESCRIPTION OF THE PREFERRED EMBODIMENTS

Figure 1:
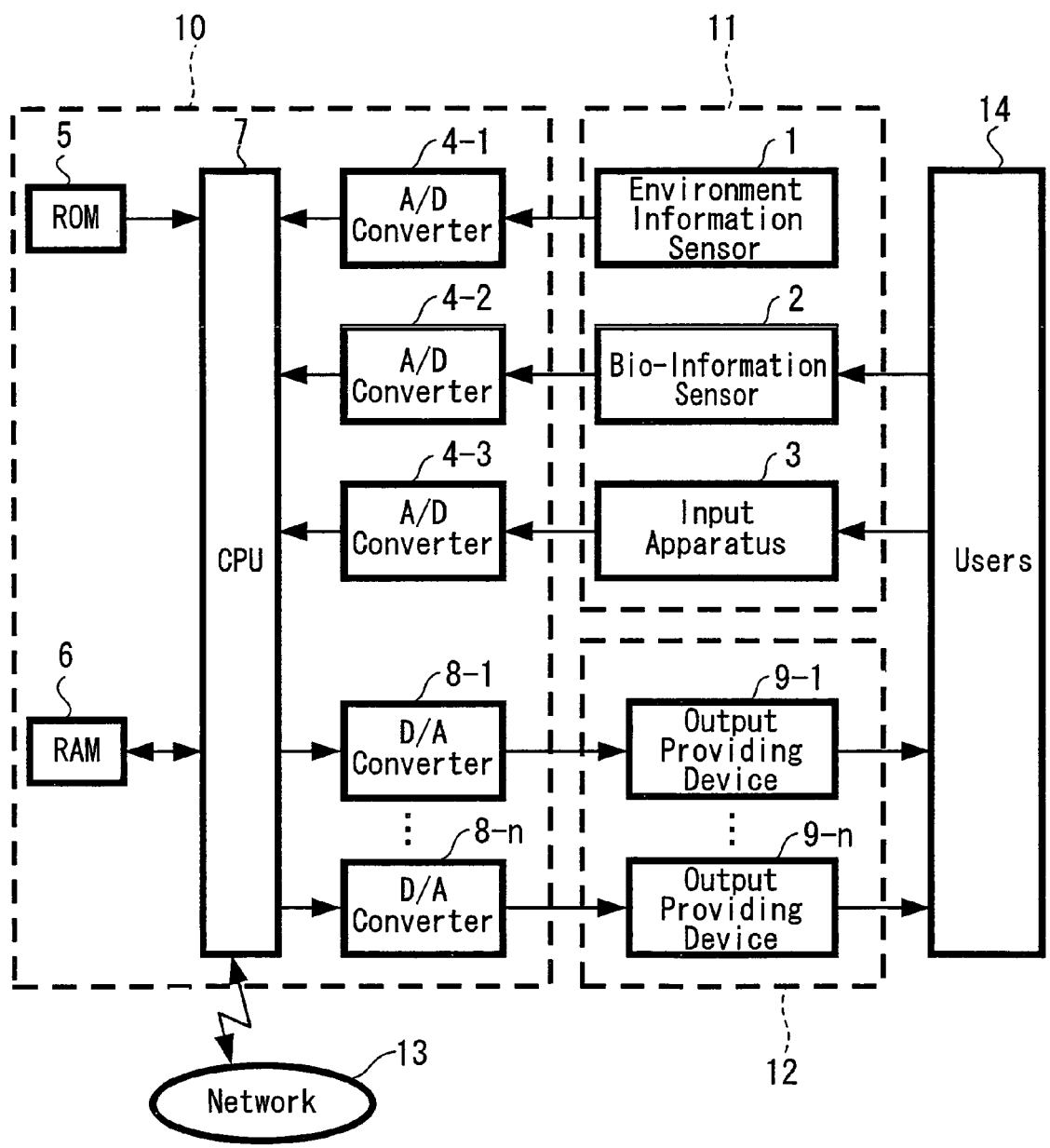
FIG. 1 is a block diagram showing a constitutional example of a control apparatus according to one exemplified embodiment of the present invention.

First, an explanation will be made with respect to a rough outline of a constitutional example according to this example with reference to FIG. 1. FIG. 1 is a block diagram showing a constitution according to an example of the present invention. This apparatus is composed of a control unit 10; an input unit 11 for inputting contents and the like which were obtained by measuring environment information and/or bio-information and by performing a user selection or a user setting of the information to the control unit 10; and a output unit 12 for outputting a result processed in the control unit 10.

In the input unit 11, an environment information sensor 1, a bio-information sensor 2, and an input apparatus 3 are provided. Here, the environment information sensor 1 is a device for measuring environment information and is, for example, a clock apparatus, a temperature gauge or a barometer. These are installed at suitable places for measuring the information of measuring objects and the measured results are inputted to the control unit 10, for example, by a method for connecting to the control unit 10 using a signal line so as to transmit thereto or by a method of a wireless transmission. The bio-information sensor 2 is a device for measuring bio-information of a user and is, for example, a heartbeat gauge, a blood pressure gauge or a brain wave measuring device. The input apparatus 3 is a device for a user to select which kind of environment information or bio-information is to be used and to perform a setting of a desirable output providing device and the like and is, for example, a keyboard, a touch panel or an audio input device.

The control unit 10 is composed of an A/D (Analog/Digital) converters 4-1, 4-2 and 4-3, a ROM (Read Only Memory) 5, a RAM (Random Access Memory) 6, a CPU (Central Processing Unit) 7 and D/A (Digital/Analog) converters 8-1 to 8-n. The A/D converters 4-1, 4-2 and 4-3 signal-convert input information from the environment information sensor 1, the bio-information sensor 2 and the input apparatus 3 from an analog signal to a digital signal and operate for transferring it to the CPU 7. The ROM 5 is a medium on which data to be used for a program describing a processing content of this apparatus and its processing are recorded. The RAM 6 is a medium on which environment information and bio-information of past utilized contents, setting contents of a user and the like are recorded together with output information at that time. The CPU 7 executes a program of the ROM 5 according to the input information from the A/D converters 4-1, 4-2 and 4-3 and the information of the RAM 6 and outputs the executed result to the D/A converters 8-1 to 8-n. The D/A converters 8-1 to 8-n signal-convert data of the executed result from a digital signal to an analog signal and transmit it to the output unit 12. It should be noted that it is possible to register programs and data to be recorded to the ROM 5 and the RAM 6 beforehand, but it is also possible to offer them externally through an external memory device, a network 13 and the like. In addition, a non-volatile memory medium such as a hard disc, a flash memory, a magneto-optical disc and the like and its driving device can be comprised additively to the ROM 5 and RAM 6 to make it possible to record aforementioned programs and various data.

In the output unit 12, output providing devices 9-1 to 9-n are provided for receiving the executed result of the control unit 10 and for offering it to a user. In the output providing apparatus, there are provided with an acoustic apparatus for proposing music; a video apparatus for proposing video; an apparatus for producing stimulation with respect to a user by means of a movement of a movable model; an apparatus for controlling the periphery environment such as temperature, humidity, illumination and smell and the like. It is made possible to offer a condition desired by a user effectively by using any of these apparatuses which stimulate the five senses of a user alone or in combination of a plurality number thereof simultaneously.

Figure 2:
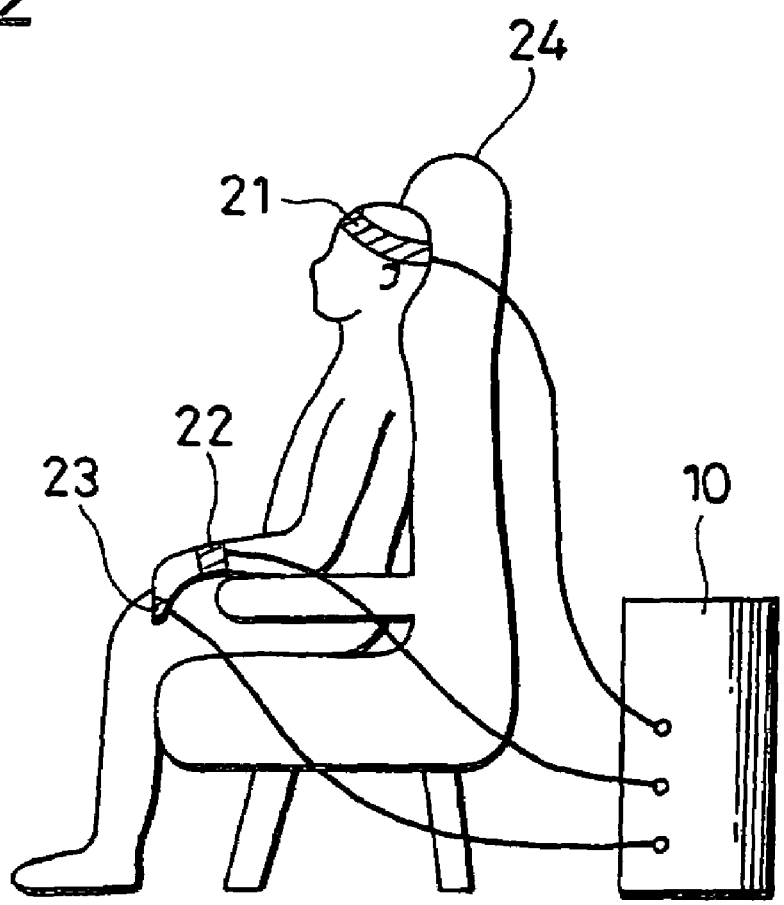
FIG. 2 is an image diagram showing one example in case of measuring bio-information of a user by a bio-information sensor according to one exemplified embodiment of the present invention.

FIG. 2 shows one example in case of measuring bio-information of a user by a bio-information sensor. A brain wave measuring apparatus 21, for example, is constituted by installing electrodes onto a head band where it is designed such that brain waves are measured by mounting it on a head portion of a user, the head band is connected to the control unit 10 through a signal line thereto and a measured result can be transmitted. Also, a blood pressure measuring apparatus 22 is constituted by installing blood pressure gauge onto a wrist band where it is designed such that blood pressure is measured by mounting it on a wrist of a user and a measured result is transmitted to the control unit 10 similarly as the brain wave measuring apparatus. Further, a heartbeat measuring apparatus 23 measures heartbeats of a user by attaching or mounting it on a finger and transmits a measured result to the control unit 10. With respect to those apparatuses, a method for mounting them on each region of a body so as to measure was explained as one example, but it is possible to mount them on other regions of a body for measuring. In addition, it is also possible to employ a method where a bio-information sensor is installed onto a sitting chair 24 on which a user sits and the like when he uses this example and bio-information such as heart rate, breathing rate or body movement is measured by contacting the body onto that portion. In addition, although not shown, it is also possible to employ a method for taking a picture of a user by a video camera so as to detect diameter change of a pupil, blinking change, body movement of a user and the like. Further, with respect to a method for transmitting the measure result from each measuring apparatus to the control unit 10, a method for directly connecting a signal line was explained, but it is needless to say that a transmission by wireless can be also employed.

Figure 3:
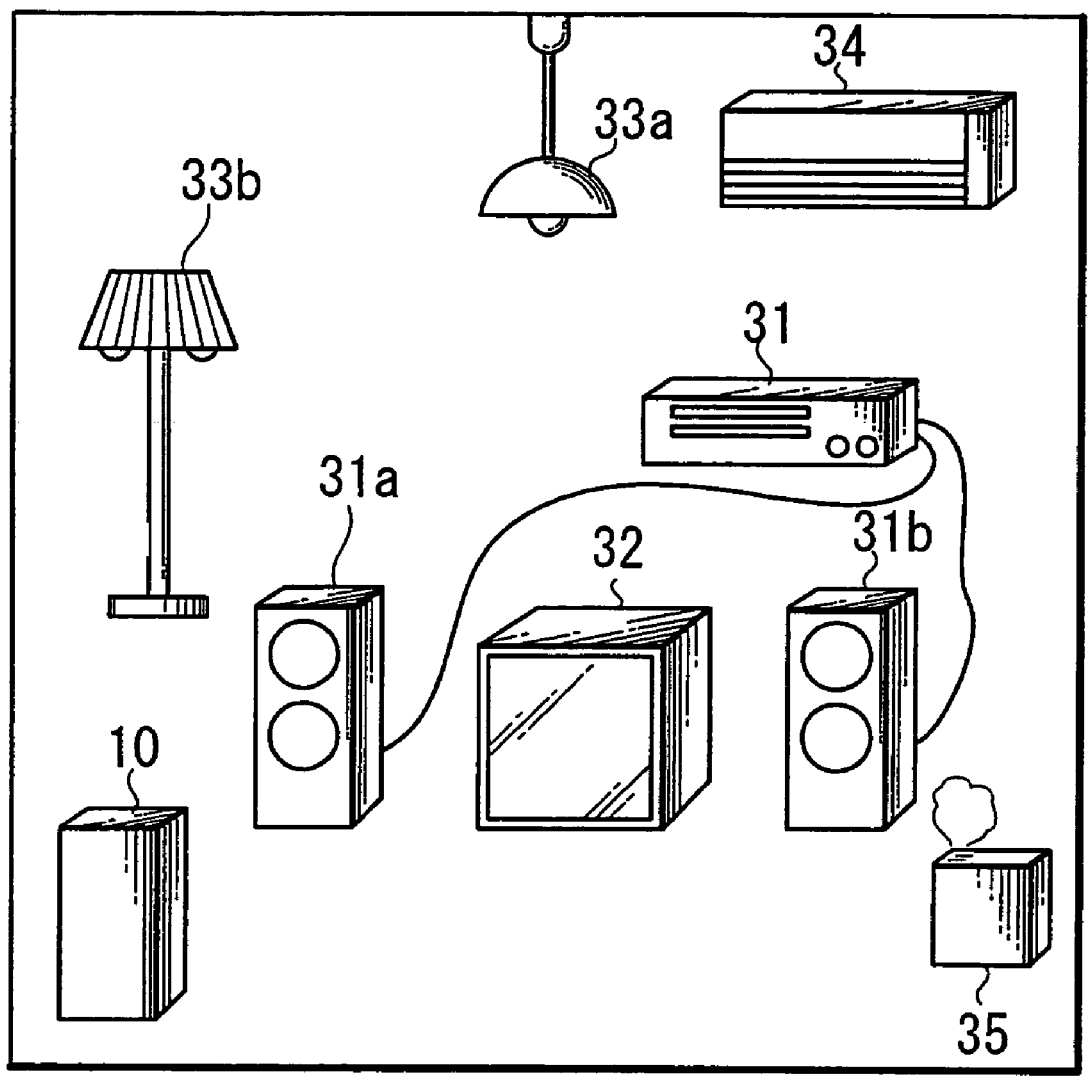
FIG. 3 is an image diagram showing one example of an output providing apparatus according to one exemplified embodiment of the present invention.

An example relating to an output providing apparatus is shown in FIG. 3. An acoustic apparatus 31 outputs a signal of a sound source produced according to the executed result of the control apparatus 10 from speakers 31a and 31b. The outputted sound can be an environment sound such as a wave sound and a singing of a bird, a sound such as a rhythmical sound having a constant rhythm which is produced and/or edited by a control apparatus or the like other than a melody which is played. The video apparatus 32 displays still pictures and moving pictures produced and/or edited by the control apparatus 10 and video signals of 3-dimensional graphic pictures and the like on a display screen such as a brown-tube display device or a plasma display or it proposes pictures by a method of projection and the like by using a cinematographic apparatus. Also, as an apparatus for controlling an environment, there are illumination apparatuses 33a and 33b for adjusting brightness, an air conditioner 34 for adjusting room temperature, a humidifier/dehumidifier 35 for adjusting humidity and the like. For the methods of transmitting control signals from the control unit 10 with respect to these output providing apparatuses, there are a method of transmitting by connecting a signal line directly, a method of transmitting by wireless and the like.

An embodied first process example using the apparatus as explained in the above will be explained with reference to a flowchart shown in FIG. 4. The process shown in FIG. 4 is a process performed mainly in the CPU 7 of the control unit 10 in a case when a user reproduces occurrences which were experience in the past by using this apparatus. It will be explained with respect to this process by taking a case as an example where music listened to in the past is reproduced together with the periphery environment, the physical condition and especially the heartbeats when it was listened to.

First, a process starts by switching on a power supply of the apparatus and the like according to a user operation relating to of this example and a utilized content which is desired is inputted from the input apparatus 3 (step S101). In the inputted items, there are a user ID for discriminating a user, environment information to be measured, information in bio-information which a user desires, an output providing apparatus which a user desires, past occurrences to be reproduced and the like. According to this example, it is assumed that room temperature is selected as environment information to be used and heartbeats are selected as bio-information. Also, an acoustic apparatus is selected as output providing apparatus and one certain affair is selected from the past utilized information which is accumulated in RAM 6 of this apparatus. Next, the CPU 7 presents the inputted setting content to a user and inquires whether or not the content is enough (step S102), and its answer is inputted from the input apparatus 3 by a user. In a case when the answer is "NO", the user is made to perform the setting once again while in case of "YES", the flow proceeds to a next process.

Next, CPU 7 instructs the environment information sensor 1 and the bio-information sensor 2 about the measuring start of the environment information and the bio-information of a user and the measuring is made to start. Then, measured results are inputted from the environment information sensor 1 and the bio-information sensor 2 to the CPU 7 through the A/D converters 4-1 and 4-2 (step S103 and step S104).

The inputted environment information and bio-information is compared with the information registered in the selected past utilized information (step S105 and step S106). Next, control signals to the respective output providing apparatuses are produced according to the compare results (step S107). In case of this example, room temperature and heartbeats are selected as information to be used so that comparison is performed with respect to these of information and control signals are produced. In a case, for example, when the room temperature at present is 18° C. while the room temperature at the past utilization was 20° C., a control signal is produced with respect to an air conditioner in the output providing apparatuses so as to raise the room temperature by 2° C. Also, in a case when heartbeats at present are 60 beats/minute while the heartbeats at the past utilization were 50 beats/minute, the output offered by the acoustic apparatus which is a selected output providing apparatus is adjusted in tune with the heartbeats. As a method for adjusting heartbeats, there is a method where, for example, when the music which was listened to in the past is reproduced, the musical tempo is first controlled to be a tempo in tune with the heartbeats and the musical tempo is made slower to be directed gradually to the objective heartbeats.

Next, the produced control signals are transmitted to respective output providing apparatuses through the D/A converters 8-1 to 8-n (step S108), and signals are made to be generated in the respective output providing apparatuses (step S109). According to this example, the room is heated by the air conditioner so as to raise the room temperature by 2° C. and further, music in tune with the heartbeats is proposed by the acoustic apparatus. Next, it is judged whether or not the output signal was decided (step S110). As a method for judging that it was decided, there are methods such as a method where the CPU 7 inquires a user whether or not the user is satisfied with the output content of the output providing apparatus at present so as to input that answer and a method where environment information or bio-information which a user selected is compared with the value registered in the past utilized information by using the CPU 7 to check whether or not they coincide with each other and if coincided, it is judged that it was decided.

Here, in a case when it is not judged that the output signal was decided, the flow returns once again to the comparing process of the environment information and the bio-information (step S105 and step S106) and the processes are repeated. In a case when it is judged that the output signal was decided, it is judged whether or not this control process may be finished (step S111) and in a case when it is not made finished, the flow returns to the signal generation of the output providing apparatus (step S109), and the processes are repeated. In a case when it is allowed to finish the process, utilized information from the process start until the end will be saved in the RAM 6 (step S112) and all processes of this apparatus are made ended after the end of the saving. Here, as a method for judging whether or not the processes can be made ended, there is a method such as, for example, a method of inquiring to a user or a method of judging whether or not the music presented by the acoustic apparatus 31 is ended and the like.

In this manner, the music and the video experienced in the past is reproduced not only for a purpose of a simple reproduction, but the periphery environment is changed such that the periphery environment and the physical condition of a user himself at that time can be also reproduced and at the same time, the music, the video and the like are made to be changed in tune with the physical condition such that a condition which a user desires can be induced.

In the process example mentioned above, it was explained with respect to a case where a user reproduces occurrences experienced in the past, but it is possible to constitute such that the physical condition of a user is made to return to a normal condition.

According to this example, the environment information and the bio-information are made to be related and then the information is organized by time and saved as accumulated information saved in the RAM 6. In addition, the information included in the same hour is further classified in correspondence with the activity condition of a human being (under a meal, under movement, under work, under sleep, under bathing and the like). The physical condition of a human being changes according to hours and activity conditions, but the livelihood of everyday is approximately definite, so that it is possible to estimate a normal physical condition of that person when he takes a certain activity at a certain time by classifying and/or organizing the environment information and the bio-information by time and by activity condition and thereafter by averaging them.

FIG. 5 is a flowchart showing a process in a case when a physical condition of a user is made to return to a normal condition. It will be explained as a second process example using this apparatus with respect to a process in a case when a physical condition of a user is made to return to a normal condition by using FIG. 5.

A user activates this apparatus and set as "return to a normal condition" in step S201. The items set here are similar as the set items in step S101 of the first process example mentioned above, so that the explanation thereof is omitted. With respect to the environment information, the bio-information and the output providing apparatus which are used in case of performing a process for returning to a normal condition, it is possible to register them in the ROM 5 or the RAM 6 beforehand. Next, the set environment information and bio-information is measured in step S203 and step S204 and inputted to the CPU 7. In step S205 and step S206, a difference between the information of a normal condition which is created from the past accumulated data and the present information is extracted and in step S207, a control signal to the output apparatus is produced so as to make the difference become zero. With respect to how to change to an objective condition by giving what kind of stimulation in what physical condition, it is determined beforehand by executing examinations targeting a lot of persons being tested with respect to the giving stimulation and the operation to its physical condition.

It will be explained as a specific example with respect to a case where it is assumed that a user who goes to bed at approximately 23 o'clock everyday activates this system at about 10 minutes past 23 o'clock and it was a time point just after the user came back home from his work and he was in a state of tension. For example, relating to the environment information, indoor illumination, room temperature and ambient noise are measured and relating to the bio-information, brain waves of a user are measured. Differences between these of measured information and accumulated values at a normal time are extracted and respective output providing apparatuses are controlled so as to make the differences become zero. When, for example, the indoor illumination is lighted and is brighter than a normal time, the light is made darker by controlling the indoor illumination apparatus and with respect to the air conditioner, it is controlled such that the room temperature becomes normal room temperature. In addition, when ambient noises such as a TV sound and the like are detected, switches of those sound sources are controlled to be turned off. Further, in a case when the measured result relating to brain waves of a user shows a state of tension, the tension is made to be released and sleeping is made to be introduced by offering relaxing sound, video, smell and the like from respective output providing apparatuses.

In this manner, it is possible to induce to a normal time condition of a user speedily without a complicated setting.

Next, it will be explained as a third process example with respect to a process of this apparatus in case of inducing to an objective condition of a user. The explanation will be done by using similar characters for respective processes as shown in the flowchart of FIG. 5.

A user activates this apparatus and selects a condition which he wants as an object in step S201 from a total list of induction-objective conditions. For example, they are such as "want to relax", "want to raise feeling", "want to lower heartbeats", "want to ease headache" and the like. Here, it is possible to register to the ROM 5 or the RAM 6 beforehand with respect to the induction-objective condition, environment information to be used for inducing to that condition, bio-information and output providing apparatuses. In addition, similarly as the second process example, with respect to how to change to an objective condition by giving what kind of stimulation in what physical condition, it is determined beforehand by executing examinations targeting a lot of persons being tested with respect to the giving stimulation and the operation to its physical condition.

It will be explained as a specific example with respect to a case where it is assumed that a user who came back from jogging activated this apparatus and set as "want to lower heartbeats". A heart rate at present is measured by the bio-information sensor in step S204 and a control signal to the output providing apparatus is produced in step S207 so as to lower it with respect to its heart rate by a fixed rate, for example, by 20% than the present value. However, it is needless to say that the heart rate to be realized should be set within a range of heart rates of a healthy person at a normal time. In a case when the setting departs from that range, the user will be notified by being alarmed or the like in step S202 which confirms the setting content and it is forbidden to proceed to subsequent processes.

In this manner, it is possible not only to propose a sound and a video in tune with the present condition of a user but also to induce the user to a situation which he wants to become from now.

It was explained in the first process example about a case where a user reproduces occurrences experienced in the past, but it is possible to constitute such that a user can experience a condition by changing a partial condition thereof to his desirable condition where the condition does not coincide with the past condition completely.

Therefore, it will be explained as a fourth process example with respect to a case according to this apparatus where a user reproduces occurrences experienced in the past by changing a part thereof. The explanation will be done by using similar characters for respective processes as shown in the flowchart of FIG. 4.

Similarly as the first process example, a user selects a condition which he wants to reproduce in step S101 from a total list of the accumulated past utilized information and selects environment information, bio-information and output providing apparatuses. Further, it will be set with respect to the information which the user wants to change from the past condition in the selected environment information and bio-information and with respect to the target value thereof. In a case, for example, when the past room temperature was 20° C. and now is 18° C. and assuming that it is all the same with respect to other information and only the room temperature is desired to become 25° C., a target room temperature of 25° C. is made set. The environment information and the bio-information at present are compared with the selected past information in step S105 and step S106, and a control signal to the output apparatus is produced in step S107 so as to make that difference become zero. At this time, in a case when there is a target value changed from the past data, it is to be controlled so as to make the difference between the target value and the present value become zero. According to the present example, for example, a control signal is produced with respect to the air conditioner so as to raise the room temperature by 7° C., because the room temperature at present is 18° C. and the target room temperature is 25° C.

In this manner, it is possible to enjoy a sound, a video and the like experienced in the past according to a desirable condition of a user which is not definitely the same condition as the past one.

It should be noted that the invention is not limited by the above mentioned exemplified embodiments and it is possible to use arbitrary multiple combination of general-use apparatuses with respect to the environment information sensors and bio-information sensors, and it is also possible to constitute such that all of the sensors installed beforehand are to be used without a selection of a user. In addition, any apparatus is enough for the output providing apparatuses other than the above mentioned exemplified embodiments if it can give stimulation to a user and if its operation is controllable by a control signal from the control unit 10. Further, the explanation of the present invention was done mainly with respect to cases of indoor use, but it is possible to realize similar effects outdoors and in a vehicle under movement in case of mobile output providing apparatuses such as a portable acoustic apparatus by selecting portable kinds of environment information sensors and bio-information sensors.

According to the present invention, it becomes possible to offer a condition which a user desires speedily by using environment information and bio-information. In addition, it is possible not only to offer a sound and a video in tune with a physical condition at present but also to reproduce a condition experienced in the past by accumulating and utilizing conditions experiences in the past. Further, by using one or multiple combination of other apparatuses than acoustic apparatuses and video apparatuses additively, it becomes possible to stimulate human five senses in a comprehensive way so as to induce to an objective physical condition more speedily than a case where an acoustic apparatus, a video apparatus and/or the like is used alone.

Having described preferred embodiments of the invention with reference to the accompanying drawings, it is to be understood that the invention is not limited to those precise embodiments and that various changes and modifications could be effected therein by one skilled in the art without departing from the spirit or scope of the invention as defined in the appended claims.

What is claimed is:

1. A control apparatus comprising:
   setting means for enabling a user to select a desired bio-information of the user to be measured and a desired environment information to be measured;
   first input means for inputting the selected bio-information;
   second input means for inputting the selected environment information; and
   control means for comparing the selected bio-information which was previously obtained with the selected bio-information currently obtained from said first input means to obtain bio difference information, for comparing the selected environment information which was previously obtained with the selected environment information currently obtained from said second input means to obtain environment difference information, and for controlling the environment in accordance with the bio difference information and the environment difference information.

2. The control apparatus according to claim 1 further comprising reproducing means for reproducing a video signal and/or an audio signal, wherein said control means controls a reproducing condition of the video signal and/or the audio signal.

3. The control apparatus according to claim 1, wherein the bio-information inputted from said first input means is one or more of information showing heartbeats, pulse-beats, breathing, blood pressure, a blood oxygen saturation, electrocardiograms, brain waves, sweating of skin, galvanic skin response, body movement, a magnetoencephalography, an electro-myography, body surface temperature, diameter size of a pupil, micro-vibration or biochemical reaction.

4. The control apparatus according to claim 1, wherein the environment information inputted from said second input means is one or more of information relating to date and hour, lunar age, ambient temperature, humidity, weather, atmospheric pressure and the ebb and flow of tide and ambient environment information relating to ambient noise, room temperature or a smell.

5. A control method comprising:
   an enabling step for enabling a user to select a desired bio-information of the user to be measured and a desired environment information to be measured;
   a first step for inputting the selected bio-information;
   a second step for inputting the selected environment information; and
   a control step for comparing the selected bio-information which was previously obtained with the selected bio-information currently obtained in said first step to obtain bio difference information, for comparing the selected environment information which was previously obtained with the selected environment information currently obtained in the second step to obtain an environment difference information, and for controlling the environment in accordance with the bio difference information and the environment difference information.

6. The control method according to claim 5 further comprising a reproducing step for reproducing a video signal and/or an audio signal, wherein a reproducing condition of the video signal and/or the audio signal is controlled in cooperation with said control step.

7. The control method according to claim 5, wherein the bio-information inputted from said first step for inputting is one or more of information showing heartbeats, pulse-beats, breathing, blood pressure, a blood oxygen saturation, electrocardiograms, brain waves, sweating of skin, galvanic skin response, body movement, a magnetoencephalography, an electro-myography, body surface temperature, diameter size of a pupil, micro-vibration or biochemical reaction.

8. The control method according to claim 5, wherein the environment information inputted from said second step for inputting is one or more of information relating to date and hour, lunar age, ambient temperature, humidity, weather, atmospheric pressure and the ebb and flow of tide and ambient environment information relating to ambient noise, room temperature or a smell.

9. The control apparatus according to claim 1, further comprising:
   memory means for storing the bio-information inputted from said first input means and the environment information inputted from said second input means in a corresponding condition.

10. The control method according to claim 5, further comprising:
    a storing step for storing the bio-information inputted from said first step for inputting and the environment information inputted from said second step for inputting in a corresponding condition.

* * * * *